United States Patent [19]

Meyer et al.

[11] Patent Number: 4,992,567

[45] Date of Patent: Feb. 12, 1991

[54] ALKYLENE OXIDE PRODUCTION USING VAPOR PHASE OXIDATION OF AN ALKANE OR OLEFIN IN MOLTEN SALT AND RECIRCULATION OF ALDEHYDE BY-PRODUCTS

[75] Inventors: James L. Meyer, Lake Charles; Pennington, B. Timothy, Sulphur, both of La.

[73] Assignee: Olin Corporation, Cheshire, Conn.

[21] Appl. No.: 362,553

[22] Filed: Jun. 7, 1989

[51] Int. Cl.$^5$ ............................................. C07D 301/06
[52] U.S. Cl. ..................................... 549/532; 549/533; 549/523
[58] Field of Search ........................ 549/523, 532, 533

[56] References Cited

U.S. PATENT DOCUMENTS

| | | | |
|---|---|---|---|
| 2,530,509 | 11/1950 | Cook | 549/523 |
| 3,132,156 | 5/1964 | Lemon et al. | 549/523 |
| 4,785,123 | 11/1988 | Pennington | 549/523 |

FOREIGN PATENT DOCUMENTS 968364  5/1975  Canada .

*Primary Examiner*—Richard L. Raymond
*Assistant Examiner*—Amelia A. Owens
*Attorney, Agent, or Firm*—Donald M. Papuga

[57] ABSTRACT

A continuous process for the vapor phase oxidation of an alkane or olefin in molten salt catalyst to produce alkylene oxides in increased yields while reducing or substantially eliminating the formation of aldehyde by-products. The process involves the continuous separation and recirculation of aldehydes, normally formed in the oxidation reaction, back into the vapor phase oxidation reaction for co-oxidation to form carbon-oxygen gases while increasing the olefin selectivity to alkylene oxide.

14 Claims, No Drawings

ALKYLENE OXIDE PRODUCTION USING VAPOR PHASE OXIDATION OF AN ALKANE OR OLEFIN IN MOLTEN SALT AND RECIRCULATION OF ALDEHYDE BY-PRODUCTS

This invention relates generally to alkylene oxide production and, more specifically, to a method involving a vapor phase reaction of olefins in molten salt in which the yield of alkylene oxide is increased and the yield of aldehyde by-products is reduced.

Alkylene oxides (vicinal epoxy alkanes), and particularly propylene oxide, are very valuable and widely used chemicals. They have been polymerized with a wide variety of monomers to yield polymers which are useful in coating compositions and in the manufacture of molded articles. Alkylene oxides have also been reacted with alcohols to yield monoalkyl ethers which have utility as solvents in many commercial processes and which are useful as components for synthetic turboprop and turbojet lubricants.

There are many methods known in the art, for the production of alkylene oxides and, most notably, propylene oxide. One of the oldest methods is the so-called "chlorohydrin process" which involves the reaction of chlorine and water to form hypochlorous acid which is then reacted with propylene to form propylene chlorohydrin. The propylene chlorohydrin is then dehydrohalogenated to yield propylene oxide. Another method to obtain propylene oxide is by the liquid phase oxidation of propylene with organic peracids. Still another method involves the liquid phase oxidation of propylene with t-butyl hydroperoxide and/or ethylbenzene hydroperoxide.

The aforementioned known methods have serious disadvantages associated therewith. For example, the "chlorohydrin process" requires the use of chlorine which is relatively expensive and corrosive in nature, requiring special handling and expensive equipment. Additionally, the chlorohydrin saponification to propylene oxide consumes alkali chemicals such as caustic soda or lime, producing a large aqueous waste stream containing chloride salts, which require costly treatment prior to discharge from the plant. The oxidation of propylene with peracids is a potentially dangerous operation and expensive equipment is needed to guard against potentially explosive hazards when working with the peracids. Another disadvantage of this method is the high cost of peracids. The t-butyl hydroperoxide and ethylbenzene hydroperoxide processes have the disadvantages of being capital-intensive, multi-step, rather complicated processes. Furthermore, these processes require co-feedstocks of isobutane or ethylbenzene, thus constraining the practical utility of the processes for propylene oxide manufacture.

Another method which has received considerable attention in the literature is the direct oxidation of hydrocarbons with an oxygen-containing gas. This method suffers from the disadvantage that it is not specific for the production of alkylene oxides but produces a variety of other compounds including acids, esters, ethers, and oxides of carbon including carbon monoxide and carbon dioxide. The reaction does, however, possess two attributes which recommend it highly for commercial utilization, i.e., inexpensiveness of starting materials and simplicity of operation. It is primarily for these reasons that much attention in recent years has been directed to improvements in methods for the production of alkylene oxides from the direct oxidation of hydrocarbons even though the producer must necessarily contend with the concurrent production of a variety of undesired products.

By way of illustration, the prior art methods which attempted to produce propylene oxide by the oxidation of propane such as that disclosed in U.S. Pat. No. 2,530,509, assigned to Linde Air Products Company, were only partially successful. The majority of the prior art methods used conventional vertical columns and differed from each other by variations in lengths and diameter of the column, temperature, pressure etc. However, all of these methods suffered one common disadvantage—the temperature of the reactants varied throughout the length of the column.

The temperature variations are easily explained since the oxidation reactions are exothermic and the amount of heat evolved differs with each reaction which is taking place. Thus, at various increments along the tube, conditions existed which favored the direction of the oxidation to products other than propylene oxide. These prior art methods necessitated the use of elaborate and expensive cooling apparatus.

Further developments in the art constituted attempts to maximize the desired olefin oxide production while minimizing by-product formation. For example, U.S. Pat. No. 3,132,156, assigned to Union Carbide Corporation, discloses the vapor phase oxidation of saturated aliphatic hydrocarbons to olefin oxides. The method described in the '156 patent is said to provide enhanced olefin oxide production as high as 46.2 lbs per 100 lbs of $C_3$ consumed which calculates to be about 33 percent (molar) selectivity. While this level of selectivity constituted an improvement, it remains less than might be desired from a commercial standpoint.

The use of a liquid phase co-oxidation process for the production of alkylene oxides is known in the prior art. By way of illustration, Canadian Patent No. 992,974, issued July 13, 1976, discloses such a process involving the reaction of an admixture of a C3 to C22 olefin, an aldehyde, and an oxygen-containing gas in a benzene medium under specified reaction conditions. However, the process disclosed in this patent does not provide as high a selectivity to alkylene oxide from the olefin reactant as might be desired.

A molten salt process for producing alkylene oxides is disclosed in commonly-assigned Pennington U.S. Pat. No. 4,785,123 issued Nov. 15, 1988, and it is an objective of the present invention to modify the process of said Patent in order to provide a new method which substantially increases the yield or level of selectivity of alkylene oxides produced thereby. The Pennington Patent discloses that the volume of olefin introduced to the molten salt reaction medium may be reduced by about 25% and replaced with a diluent gas, such as nitrogen or a mixture of oxidation by-product gases such as acetaldehyde, methane and carbon dioxide obtained from the downstream alkylene oxide purification operation, in order to reduce the high partial pressure of the olefin and prevent thermal cracking of the olefin.

Two major problems exist in the known molten salt oxidation processes for converting olefins such as propylene to alkylene oxides such as propylene oxide, namely the lower than desired selectivity to alkylene oxide, which is about 45%, and the larger than desired selectivity to aldehyde formation, such as acetaldehyde, which is from about 18% to 25%.

Known liquid phase processes which co-oxidize propylene oxide and acetaldehyde require the use of large amounts of acetaldehyde, and produce large quantities of acetic acid by-product whereas the desired end-product is propylene oxide. The overall propylene oxide selectivity of such processes is not increased but acetaldehyde is converted into acetic acid, which is a more marketable material.

The present invention is based upon the discovery that the yield of alkylene oxide produced by known molten salt oxidation processes can be substantially increased by a novel continuous recirculation process in which the advantages of the molten salt process are enhanced by isolating and recirculating the aldehyde by-products, whereby the overall molar selectivity of olefin to alkylene oxide is substantially increased to at least about 60%, undesirable, low value aldehydes are substantially completely consumed and the volume of other low value by-products, such as carbon monoxide and carbon dioxide, is substantially reduced.

The present invention relates to a continuous recirculation process for producing an alkylene oxide comprising:
(a) reacting an alkane or olefin having from 3 to 22 carbon atoms per molecule, or mixture thereof, with oxygen or an oxygen-containing gas, said alkane or olefin and oxygen or oxygen-containing gas being gaseous reactants, by contacting said gaseous reactants with a bath, stream, spray or mist of at least one molten nitrate or chloride salt catalyst, said catalyst being present in an amount sufficient to absorb any heat generated during said reaction while maintaining an essentially constant reaction temperature between about 135° C. and about 600° C. and a reaction pressure of between about 1 and about 50 atmospheres to produce an alkylene oxide and by-products comprising a substantial amount of at least one aldehyde, and
(b) separating the aldehyde from the alkylene oxide and from the other by-products, and
(c) recirculating the aldehyde in gaseous form back into the reaction mixture of step (a), with the optional addition of more of said aldehyde or mixture, to produce a continuous gaseous co-oxidation of said olefin(s) and said aldehyde(s) which substantially increases the selectivity of olefin to form alkylene oxide and reduces or eliminates the amount of aldehyde by-products.

Several factors will affect the reactant conversion to alkylene oxide and the selectivity of alkylene oxide production vis-a-vis by-product production in accordance with the process of the present invention. For example, in step (a) of the process these factors include: the contact time of the molten salt with the oxygen-containing gas, the temperature of the reactor product gases, the molten salt temperature, the molten salt catalyst composition, the feed gas temperature, the feed gas composition, the feed gas pressure, and the co-catalyst employed (if any).

The oxygen-containing gas useful as a reactant in the present invention can be any such gas. Typically, air is employed as the oxygen-containing gas based upon its ready availability. However, other oxygen-containing gases can be employed such as pure oxygen, and the use of oxygen is expected to be preferred in a commercial setting.

The olefin useful in the present invention can be broadly defined as an epoxidizable, olefinically-unsaturated hydrocarbon compound having from 3 to 22 carbon atoms, preferably from 3 to 15 carbon atoms, more preferably from 3 to 12 carbon atoms, most preferably from 3 to 10 carbon atoms. This definition is intended to include terminal olefins selected from the group consisting of monofunctional and difunctional olefins having the following structural formulas respectively:

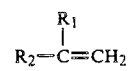

wherein $R_1$ is hydrogen or an alkyl chain, straight or branched, having 1 to 20 carbon atoms and $R_2$ is an alkyl chain, straight or branched, having 1 to 20 carbon atoms; and

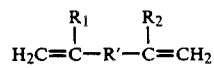

wherein $R_1$ and $R_2$ are hydrogen atoms or alkyl chains having 1 to 10 carbon atoms and $R'$ is from 2 to 10 methylene groups. The definition also includes cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

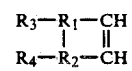

wherein $R_1$ and $R_2$ are olefin radicals having 1 to 4 carbon atoms and $R_3$ and $R_4$ represent hydrogen atoms, or one or two alkyl radicals, straight or branched chain, having 1 to 10 carbon atoms. The internal olefins are represented by the following structural formula:

wherein $R_1$ and $R_2$ are straight chain or branched chain alkyl radicals having 1 to 10 carbon atoms.

The alkanes, olefins, and mixtures thereof, useful as reactants in accordance with the present invention generally have up to, but do not exceed, 22 carbon atoms per molecule, preferably not more than 12 carbon atoms per molecule. When a straight-chain molecule is employed, it is more preferred that such molecule not have more than ten carbon atoms. When a cyclic compound is used, it is more preferred that the cyclic compound not have more than 12 carbon atoms per molecule. A preferred reactant within this group is propylene.

Representative other alkanes or olefins are butene-1, butene-2, isobutylene, pentene-1, hexene-1, pentene-2, cyclopentene and cyclooctene. Other representative olefins are 2-methylbutene-1, 3-methylbutene-1, heptene-1, octene-1, hexene-2, hexene-3, octene-2, heptene-3, pentadecene-1, octadecene-1, dodecene-2, 2-mehylpentene-3, tetramethylethylene, methylethylethylene, cyclobutene, cycloheptene, 2-methylheptene-1, 2,4,4-trimethylpentene-1, 2-methylbutene-2, 4-methylpentene-2, 2-ethyl-3-methylbutene-1, propane, isobutane, pentane, and cyclohexane.

In step (a) of the process of the present invention, the olefin gas and the gasified recycled aldehyde preferably are preheated to prevent condensation in the line delivering these gases to the reactor. Alternatively, both the oxygen-containing gas and the olefin gas and aldehyde (collectively referred to herein as "the feed gases") can be preheated to prevent condensation in any of the feed lines. However, in the absence of preheat, the molten salt will rapidly heat the feed gases up to reaction temperature. If the feed gas is preheated, it preferably is maintained at at least about 100° C. in the feed gas line(s).

The molten nitrate or chloride salt(s) catalyst is generally maintained at a temperature sufficient to keep the salt(s) in a molten condition. Preferably, the temperature is maintained between about 135° C. (275° F.) and about 600° C. (1,000° F.), more preferably between about 150° C. and about 450° C., most preferably between about 200° C. and about 400° C. during the reaction in accordance with the present invention.

The specific temperature selected is based upon the melting point of the particular molten salt chosen. For example, mixtures of molten lithium and potassium nitrate can be suitably employed at a temperature as low as about 280° F., and hence, this temperature may be employed when using lithium nitrate. In the selection of a suitable molten salt bath temperature, it is important to choose a temperature below the thermal decomposition temperature for the particular molten salt chosen. In addition, it is important to maintain a sufficient isotherm across the molten salt bath so as to avoid crust formation of the salt in the bath. Such a crust formation in the salt bath can cause localized overheating of gases trapped by the crust in the bath and an associated "runaway" oxidation reaction due to overheating of the gases in the bath. In order to maintain a bath isotherm, constant stirring of the molten salt bath is preferred. Alternatively, the molten salt can be circulated by conventional means, such as the use of internal draft tubes or external pumping loops.

The nitrate or chloride salt catalyst used may be any one of the alkali or alkaline earth salts such as lithium, sodium, potassium, rubidium, cesium, magnesium, calcium, strontium, or barium or mixtures thereof. In addition, nitrate and chloride salts can be used in mixtures with each other and/or with other salts such as bromides, carbonates, sulfates, and phosphates. Preferably, the content of the other salt(s), when present, should be restricted to less than 60 percent by weight based upon the weight of the total melt and in most cases their contents should not exceed about 25 percent of the total melt.

In step (a) the ratio of olefin and aldehyde to oxygen in the oxygen-containing gas in the reactor can vary over a wide range. However, in accordance with the present invention, it has now been found that enhanced selectivity of alkylene oxide product is achieved by maintaining a relatively low amounts of aldehyde and oxygen relative to the amount of olefin fed into the reactor. For example, when reacting propylene with oxygen in a molten potassium nitrate salt column at elevated pressure, a ratio of between about 2 and about 100 parts per volume of propylene per 1 part per volume of oxygen, e.g., about 1 to 35 volume percent oxygen to about 66 to 99 volume percent propylene is found to provide an enhanced selectivity of propylene oxide. A preferred ratio is between 4:1 and 30:1, most preferably between about 8:1 and 20:1. Another consideration in the selection of the amount of olefin to use as a feed is the high partial pressure of the olefin which in high concentrations can cause thermal cracking of the olefin reactant itself. Therefore, when conducting the oxidation reaction on certain olefins such as propylene, it is preferred to decrease the propylene to 50 to 75 volume percent and utilize an inert blanket (diluent") gas, such as nitrogen, to provide the remaining volume percent to feed gas.

According to the present invention the volume of olefin is also "cut" by the volume percent of gaseous aldehydes being recycled, and optionally by the volume percent of additional new aldehyde added with new olefin and oxygen to the reactants in step (a), for purposes of increasing the selectivity and yield to alkylene oxide while consuming the less desirable, lower value aldehyde by products.

The volume percent of the aldehyde in the feed gases is minor, i.e., from about 0.1 to about 10 volume percent of the combined volume of olefin, oxygen, nitrogen and aldehyde, more preferably between about 0.5 and 5 volume percent and most preferably between about 0.5 and 3 volume percent. Since the aldehyde is continuously oxidized to carbon monoxide and carbon dioxide in the reactor, it is necessary to add fresh amounts of the corresponding aldehyde, i.e., acetaldehyde when the olefin is propylene, to maintain the high selectivity to the alkylene oxide.

In the selection of the ratio of the volume of oxygen-containing gas relative to the volume of olefin employed in the reaction mixture, the range of ratios which might pose a flammability hazard should be avoided, as is well known. For example, when utilizing an air/propylene reactant mixture at atmospheric pressure, the range of below 7 volume percent of propylene based upon total air plus propylene should be avoided.

A co-catalyst can also be utilized in accordance with the present invention. For example, when an elemental metal, or the oxide or hydroxide thereof, is employed as a co-catalyst in conjunction with the molten salt catalyst, it is possible to lower the reaction temperature for the particular salt selected and/or enhance the selectivity or conversion to the desired olefin oxide. By way of illustration, a palladium on alumina co-catalyst or a silver co-catalyst such as silver nitrate is expected to similarly reduce the required reaction temperatures. The use of these metal co-catalysts is preferred when the reaction is conducted at atmospheric pressure. At superatmospheric pressure, an alkali metal hydroxide co-catalyst, such as sodium hydroxide, has been found to be particularly advantageous in providing enhanced selectivity to the desired product. In addition, in a continuous process employing caustic recycle, the alkali metal hydroxide is expected to enhance the desired product distribution by removing by-product carbon dioxide by forming alkali metal carbonate.

If used, the co-catalyst is generally employed in a catalytically effective amount, generally in an amount of less than about 5 (preferably between about 0.5 and about 5, more preferably in an amount between about 0.5 and about 3) weight percent based on the total amount of co-catalyst plus molten salt catalyst.

The molten salt catalyst in which the co-catalyst (if used) is suspended or dispersed, helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

Typically, the molten salt(s) is employed in an amount on a weight basis of between about 5 times and about 100 times (preferably between about 5 times and about 50 times) the total weight of the reactants employed.

The molten salt(s), in addition to functioning as a catalyst and as an isothermal medium for the co-catalyst, if used, also serve as a temperature regulator. More specifically, the molten salt(s) have a high heat absorption capacity, enabling them to absorb large quantities of heat during the exothermic oxidation reaction while maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperatures.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture. Another preferred molten mixture is a mixture of sodium, lithium and potassium nitrate salts, preferably in a ratio of between about 10 and about 30 weight percent of lithium nitrate and between about 15 and about 75 weight percent of sodium nitrate based on the total amount of the mixture. Chloride salt mixtures such as the potassium, cuprous and cupric chlorides also provide excellent results.

One method of contacting the gaseous reactants in the presence of the molten nitrate salt is by bubbling the reactants through a bath of the molten salt. If the gaseous reactants are bubbled into the bottom of the bath or column containing the molten salt, the contact time of the reactants with the molten salt catalyst is equal to the "rise time" of the reactants through the bath or column. Thus, the contact time can be increased by increasing the length of the molten salt bath or column. An alternate method of contacting the gaseous reactants in the presence of the molten salt would be to pass the gaseous reactants through a reactor countercurrently to a spray or mist of the molten salt. This latter method is preferred since it provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gas-liquid contact in reaction systems may also be employed.

The olefin feed gas(es) can be passed into the molten salt-containing reactor using a separate stream (e.g. feed tube) from the stream(s) delivering the aldehyde and oxygen-containing gas to the reactor. Alternatively, the reactant gases can be fed into the reactor together in a single stream. In a preferred embodiment of the present invention, two co-axially-mounted feed gas tubes are employed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

The segregated and recycled gaseous aldehyde or aldehyde mixture can be fed directly to the salt bath by its own feed tube or said feed tube can be connected to an aldehyde supply tube through which the recycled aldehyde is combined with new aldehyde to form a uniform supply which is fed directly to the reactor or to the olefin or oxygen supply tubes.

If a molten salt bath is used, the feed gases are preferably bubbled into the molten salt-containing reactor using a sparger. If used, the sparger is preferably positioned in the molten salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas(es) in the other tube will maintain sufficient pressure to keep the molten salt from backing up into the unpressurized feed gas tube.

This process is run in a continuous operation. The order of introduction of the reactants is determined by the operator based on what is most safe and practical under prevalent conditions. Generally, the desirability of avoiding flammable gas mixture throughout the reaction and subsequent product separation systems will dictate the desired procedures.

Step (a) of the process can be carried out by feeding a mixture of olefin, aldehyde, inert gas, and oxygen into a reaction vessel containing the molten salt. The reaction vessel can be glass, glass-lined metal, or made of titanium. For example, a glass-lined stainless steel autoclave can used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation helps prevent crust formation of the salt(s) at the head gas/salt interface in the reactor. This can be accomplished by using a mechanically stirred autoclave, a multi-point injection system, or a continuous process, e.g , with a loop reactor wherein the reactants are force circulated through the system. Sparging can also be used. In the subject process, it is found that increased rates of reaction are obtained by good gas-liquid contact provided by agitation of the molten salt/gas mixture.

Step (a) is suitably carried out at atmospheric or superatmospheric pressure. Typically, the process is effected at superatmospheric pressures of up to about 100 atmospheres, preferably between about 1 atmosphere and about 50 atmospheres, more preferably between about 1 atmosphere and about 35 atmospheres. The most preferred pressure range is between about 1 and about 25 atmospheres.

It is to be understood that by-products of the aldehyde oxidation are also produced during the reaction. Some dehydrogenation of the feed is also effected, particularly at higher temperatures within the hereinabove noted temperature range, and therefore, the reaction conditions are generally controlled to minimize such production. The separation of the resulting by-products in order to recover the desired alkylene oxide product and segregate the aldehydes for recirculation can be effected by a wide variety of well-known procedures such as: absorption in water followed by fractional distillation, absorption, and condensation.

Step (c) of the present process involves recirculating the substantial amount of aldehyde by-product, isolated in step (b) by fractional distillation of the gaseous by-product of step (a), for reintroduction into step (a) in combination with additional olefin, aldehyde and oxygen or an oxygen-containing gas, in order to co-oxidize the aldehyde and the additional amount of olefin, such as propylene, with greater than 90% selectivity to alkylene oxide, such as propylene oxide. In this manner the overall yield or selectivity to alkylene oxide is substantially increased, which is the main objective of the present process, while the large amount of aldehyde, such as acetaldehyde, normally left over as a by-product of the gas phase molten salt oxidation of propylene is recirculated and further co-oxidized to form carbon monoxide and carbon dioxide products. Thus the selectivity to alkylene oxide is increased to a rate of 60% or more, the amount of aldehyde by-product is consumed and less objectionable by-products are produced.

The co-oxidation reaction of Step (a) involves the indirect oxidation of the olefin by way of the oxidation of a portion of the aldehyde to a free radical intermediate which epoxidizes the olefin to form the alkylene oxide and carbon oxides. Such vapor phase co-oxidation processes for producing alkylene oxides from olefins and aldehydes in a molten salt catalyst are novel and are only practical in cases where the aldehyde by-products are recycled to eliminate further purification and marketing of these lesser valued products.

The particular aldehydes produced in the vapor phase reaction of step (a) depend upon the particular olefin(s) used therein. In the case of propylene, being oxidized to propylene oxide, the molar selectivity to acetaldehyde is substantial, in the area of 20-25%, with a smaller selectivity to acrolein, propionaldehyde and formaldehyde, in the area of 1-5% each. The maximum benefit in increasing the molar selectivity and yield of the alkylene oxide is gained if the fresh aldehyde, added to step (a) with the recycled aldehyde, is the same as the recycled aldehyde produced in greatest quantity in the reaction of step (a), i.e., acetaldehyde in cases where the olefin used in step (a) is propylene.

The reaction of step (a) results in the oxidation of a major amount of the aldehydes present in the vapor phase salt reactor in step (a), generally from 70% up to over 90% by weight thereof, provided that the volume percent of the gaseous aldehyde in the feed gases is maintained within the range given hereinbefore. The feed gases are passed through the molten salt catalyst, such as by introduction at the bottom of a molten salt column reactor in which the salt is flowing downward while the gases flow upward therethrough to a gas/liquid separator in which the reacted feed gases are separated from the liquid salt composition. The reacted gases pass to any conventional means for separating the alkylene oxide and aldehydes from each other and from the other by-products, after which the aldehydes are recycled back into the feed gas supply to the reactor and the alkylene oxide is further purified for storage as the desired end product. The other by-products, mainly carbon-oxygen gases such as carbon monoxide and carbon dioxide, are safely discarded.

The following examples are intended to illustrate, but in no way limit the scope of the present invention.

EXAMPLE 1

The salt flow reactor consists of a salt circulation loop and a gas flow through loop. The reactor section consists of $\frac{1}{4}$ inch 304 S. S. pipe 25 feet in length coiled in a three inch diameter coil and packed with static mixing elements throughout. Feed gas containing 50 volume percent propylene, 12 volume percent oxygen, 36 volume percent nitrogen, and 2 volume percent acetaldehyde at a STP flow rate of 4000 cc/min is directed at 358 psig cocurrently through the reactor section with the flowing molten salt. The reactor pressure is maintained using a back pressure regulator. The salt flow through the reactor section is 0.50 GPM of molten salt consisting of 30 mole percent lithium nitrate, 50 mole percent potassium nitrate, and 20 mole percent sodium nitrate (melting point 140° C.). The cocurrent flow of molten salt and reaction gases passes through the reactor to a gas-liquid separator, which sends the salt downward to the salt circulation loop and sends the reactor off gas overhead to a condensate trap for condensible ingredients such as water and water-soluble materials such as propylene oxide and the aldehydes, the main one of which is acetaldehyde. The unreacted propylene and the aldehydes are separated by fractional distillation and are recirculated back into the feed gas supply for mixture with sufficient fresh acetaldehyde to maintain the 2 volume percent aldehyde content in the reaction medium of step (a). The flowing salt is maintained at 200 degrees C and the feed gas and salt are allowed to flow for 30 minutes, after which time the reaction is stopped by switching over to nitrogen feed gas. Analysis of reaction off gas and condensate samples by GC and GC/MS methods shows that 80% of the acetaldehyde is oxidized to carbon dioxide and carbon monoxide and that the selectivity to propylene oxide is increased to 68 percent versus 57 percent in the absence of acetaldehyde in the feed gas. The per pass conversion of propylene is found to be 14 percent versus 10 percent in the absence of acetaldehyde in the feed gas.

EXAMPLE 2

Propylene is oxidized in a similar manner as in Example 1, except that the reactor type was changed. The reactor consists of a two inch diameter pipe three feet in length packed with 2$\frac{1}{2}$ feet of wire gauze mixing elements from the bottom up. This reactor is operated in a countercurrent flow mode with molten salt introduced at the top of the reactor and feed gas at the bottom of the reactor. Feed gas containing 50 volume percent propylene, 12 volume percent oxygen, 36 volume percent nitrogen, and 2 volume percent acetaldehyde at a STP flow rate of 4000 cc/min is injected at 355 psig countercurrently through the reactor section with the flowing molten salt going down and the gas going up to the separation apparatus in which unreacted propylene and the aldehydes, mainly acetaldehyde, are isolated and recirculated back into the feed gas supply to the reactor, with fresh acetaldehyde, to maintain the desired 2 percent volume percent aldehyde content. The reactor pressure is maintained using a back pressure regulator. The salt flow through the reactor is 0.60 GPM and the composition of the salt is the same as in Example 1. The flowing salt is maintained at 200 degrees C and the feed gas and salt are allowed to flow for one hour, after which time the reaction is stopped by switching over the nitrogen gas to blanket the reactor and the salt flow to the reactor is stopped. Analysis of the off gas and condensate samples by GC and GC/MS methods show that 90% of the acetaldehyde is oxidized to carbon dioxide and carbon monoxide and that the propylene oxide selectivity is 65% versus 53% without the acetaldehyde in the feed gas. The per pass conversion of propylene is 15% versus 10% without the acetaldehyde.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

What is claimed is:

1. A continuous vapor phase process for producing an alkylene oxide comprising:
   (a) reacting an alkane or olefin having from 3 to 22 carbon atoms per molecule, or mixture thereof, with oxygen or an oxygen-containing gas, said alkane or olefin and said oxygen or oxygen-containing gas being gaseous reactants, by contacting said gaseous reactants with a bath, stream, spray or mist of at least one molten nitrate or chloride salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres to produce an alkylene oxide and by-products comprising substantial amounts of at lease one aldehyde;
   (b) separating said aldehyde from said alkylene oxide and the other by-products, and
   (c) recirculating said aldehyde in gaseous form back into the gaseous reactants in step (a) to produce a vapor phase co-oxidation reaction in which the overall yield of alkylene oxide is substantially increased, the aldehyde by-products are substantially reduced or eliminated.

2. A process according to claim 1 in which said alkylene oxide comprises propylene oxide, said olefin comprises propylene, and said aldehyde comprises acetaldehyde.

3. A process according to claim 1 in which said alkane or olefin and said oxygen-containing gas are present in step (a) in a volume ratio between about 2:1 and 100:1.

4. A process according to claim 1 in which the reaction of step (a) is conducted at a temperature between about 200° and 400° C. and under a pressure between about 1 and 25 atmospheres.

5. A process according to claim 1 which comprises bubbling said alkane or olefin and said oxygen or oxygen-containing gas reactants through a bath of said molten salt catalyst.

6. A process according to claim 1 in which the alkylene oxide and aldehyde produced according to step (a) are separated by absorption in water followed by fractional distillation, and the aldehyde is recirculated back to step (a) in combination with an additional amount of said aldehyde to maintain the aldehyde content at between about 0.5 and 5 volume percent of the total gaseous ingredients.

7. A process according to claim 6 in which the aldehyde produced according to step (a) is continuously recycled back into the gaseous reactants of step (a) to produce substantially complete conversion of the aldehyde.

8. A process according to claim 1 in which the volume percent of aldehyde in step (a) is between about 0.5 to 5.

9. A process according to claim 8 in which said volume percent is between about 0 5 to 3.

10. A process according to claim 1 in which said gaseous reactants are present as components of a feed gas which also includes a substantial volume percentage of an inert diluent gas.

11. A process according to claim 10 in which said diluent gas is nitrogen.

12. A continuous process according to claim 1 for producing propylene oxide comprising:
    (a) reacting propylene with oxygen or an oxygen-containing gas, said propylene and said oxygen or oxygen-containing gas being gaseous reactants, by contacting said gaseous reactants with a bath of at least one molten salt catalyst, said catalyst being present in an amount sufficient to absorb any heat generated during said reaction while maintaining an essentially constant reaction temperature, said reaction being conducted at a reaction temperature of between about 200° C. and about 450° C. and a reaction pressure of between about 10 and 30 atmospheres to produce propylene oxide and acetaldehyde,
    (b) separating said acetaldehyde from said propylene oxide, and
    (c) recirculating said acetaldehyde in gaseous form back into the gaseous reactants of step (a) to produce a vapor phase co-oxidation reaction in which the overall yield of propylene oxide is substantially increased, the amount of acetaldehyde is substantially reduced or eliminated and by-products comprising carbon monoxide and carbon dioxide are produced.

13. A process according to claim 12 in which additional acetaldehyde is also supplied in gaseous form to the gaseous reactants of step (a) to maintain the volume percentage of the total aldehyde content at a predetermined level.

14. A process according to claim 12 in which said propylene oxide and said acetaldehyde are separated by fractional distillation means.

* * * * *